United States Patent [19]

Hewka et al.

[11] Patent Number: 5,163,963

[45] Date of Patent: Nov. 17, 1992

[54] PROSTHETIC IMPLANT WITH SPACERS HAVING TAPERED TRAILING EDGES

[75] Inventors: Leda C. Hewka, Philadelphia, Pa.; Perry A. Geremakis, South Bend, Ind.; Mark B. Lester, Warsaw, Ind.; Jack E. Parr, North Webster, Ind.

[73] Assignee: Zimmer, Inc., Warsaw, Ind.

[21] Appl. No.: 832,182

[22] Filed: Feb. 6, 1992

Related U.S. Application Data

[63] Continuation of Ser. No. 662,089, Feb. 28, 1991, Pat. No. 5,116,380.

[51] Int. Cl.⁵ .............................. A61F 2/36; A61F 2/30
[52] U.S. Cl. ........................................... 623/23; 623/18
[58] Field of Search ....................... 623/16, 18, 20, 22, 623/23

[56] References Cited

U.S. PATENT DOCUMENTS

| | | |
|---|---|---|
| 4,566,138 | 1/1986 | Lewis et al. ....................... 623/16 X |
| 4,783,192 | 11/1988 | Wroblewski et al. ............. 623/23 X |
| 4,795,472 | 1/1989 | Crowninshield et al. ......... 623/18 X |
| 4,997,448 | 3/1991 | Filer ....................................... 623/23 |

FOREIGN PATENT DOCUMENTS 3609120  9/1987  Fed. Rep. of Germany ........ 623/16

Primary Examiner—Ronald Frinks
Attorney, Agent, or Firm—Todd A. Dawson

[57] ABSTRACT

A prosthetic implant for insertion into a cement filled intramedullary canal including a plurality of spacers formed from PMMA. The spacers include a body having a frontal portion and a trailing portion. The body of the spacers narrowing with distance from said frontal portion toward said trailing portion. The narrowing body of the spacers interrupting the flow of cement along the implant body as the body is inserted into a cement filled intramedullary canal. The narrowing trailing portion of the spacers cause the cement flow to smoothly re-attach to the implant body without creating substantial disturbances or vortexes in the cement.

6 Claims, 1 Drawing Sheet

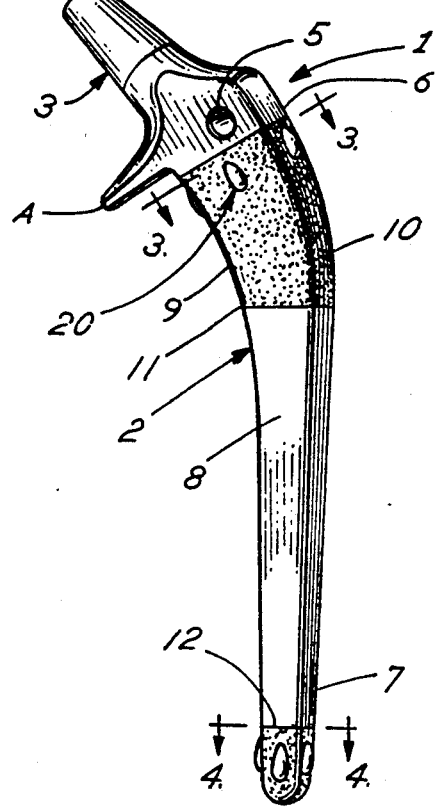
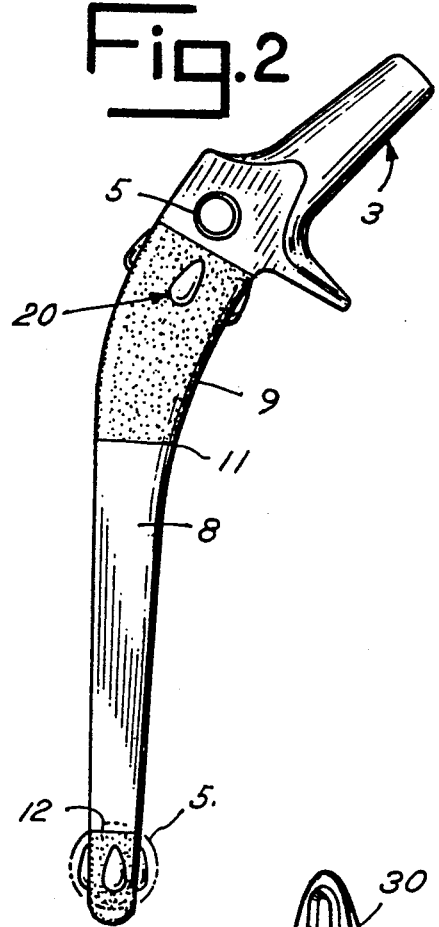
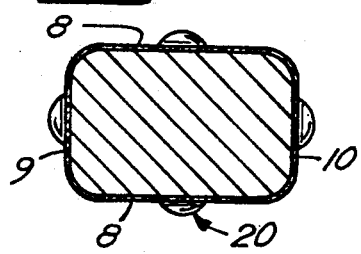
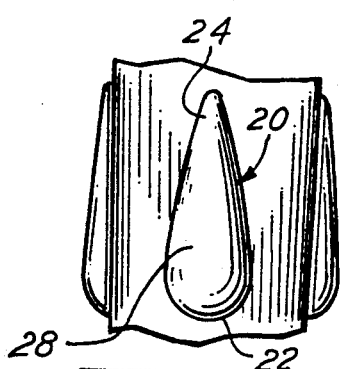
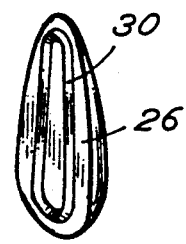
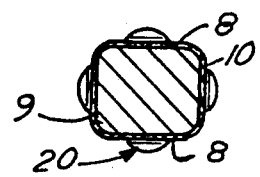
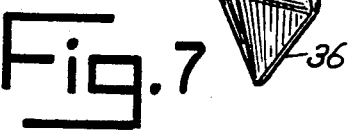

PROSTHETIC IMPLANT WITH SPACERS HAVING TAPERED TRAILING EDGES

This is continuation Ser. No. 07/662,089 filed Aug. 29, 1991, now U.S. Pat. No. 5,116,380 granted May 26, 199

BACKGROUND OF THE INVENTION

Centralizers or spacers when used with cementable prosthetic implants provide an even spacing between the implant and the supporting bone thus uniformly controlling the thickness of the cement mantle. It is know that such spacers may be formed from polymethylmethacrylate (PMMA).

Numerous types of centralizers or spacers for prosthetic hip stem implants are disclosed in the following:
Barbarito et al. U.S. Pat. No. 4,829,919;
Brown U.S. Pat. No. 4,718,909;
Meyer U.S. Pat. No. 4,549,319;
Eftekhar U.S. Pat. No. 4,404,692;
Ling et al. U.S. Pat. No. 3,793,650;
Lee et al. U.S. Pat. No. 2,104,391; and
UK Patent Application 2 216 015 - Sheenan.

Centralizers or spacers for articulated prostheses used in knees are illustrated in the following:
Engelbrecht et al. U.S. Pat. No. 4,538,305;
Frey U.S. Pat. No. 4,523,587; and
Engelbrecht et al. U.S. Pat. No. 4,268,920.

In general, the Centralizers or spacers disclosed above in conjunction with stemmed prosthetic implants require some assembly by the surgeon to connect the spacers of the implant during surgery. Further, the spacers terminate in a blunt trailing edge relative to the leading insertion end of the implant. These blunt trailing edges can cause vortices within the cement as the spacers and implant are inserted into a cement filled intramedullary canal. These vortices can cause voids adjacent the implant when the cement cures. Such voids are generally considered undesirable and may contribute to a weakened connection between the implant and the supporting bone.

SUMMARY OF THE INVENTION

The invention herein disclosed alleviates the problems discussed above by providing a prosthetic implant having spacers directly connected to the implant and having a tapered trailing portion. As the implant with spacers attached is inserted into a cement filled intramedullary canal, the smooth flow of cement along the implant is interrupted by the spacers. However, the spacers tapered trailing portion causes the cement flow to smoothly re-attach to the implant without creating vortices or eventual voids in the cement as may be experienced in the prior art spacers. The flow of cement over and about the spacers may be substantially likened to that of air flow across the upper surface of an airfoil.

The implant may include a polymer coating to improve the bond between the cement and implant. The spacers in the preferred embodiment are preferably formed from poly methyl methacrylate (PMMA) and are preferable connected to the implant by ultrasonically welding the spacers to the polymer coating.

Accordingly, it is an object of this invention to provide a novel prosthetic implant with spacers.

Another object of this invention is to provide for a prosthetic implant with spacers wherein the spacers have a tapered trailing portion.

Another object of the invention is to provide a novel prosthetic hip stem implant with a polymer coating wherein the spacers are bonded to the polymer coating.

Still another object of this invention is to provide a novel spacer for a prosthetic implant having a tapered trailing portion.

Yet other objects of the invention will become apparent from a reading of the following description taken with the accompanying drawings.

BRIEF DESCRIPTION OF THE DRAWINGS

FIG. 1 is a perspective view of a prosthetic hip implant with the spacers of the invention attached.

FIG. 2 is a side elevational view of FIG. 1

FIG. 3 is a cross-sectional view taken along line 3—3 of FIG. 1 near the proximal end of the hip stem.

FIG. 4 is a cross-sectional view taken along line 4—4 of FIG. 1 near the distal end of the implant stem.

FIG. 5 is an enlarged view of the area circled in FIG. 2 designated by the numeral 5.

FIG. 6 is a rear perspective view of the spacer illustrated in FIGS. 1-5.

FIG. 7 is an alternative embodiment of a spacer for connection to an implant.

DESCRIPTION OF THE PREFERRED EMBODIMENTS

The preferred embodiments herein disclosed are not intended to be exhaustive or to limit the application to the precise forms disclosed. Rather, they are chosen and described to best explain the invention so that others skilled in the art may utilize their teachings.

Referring now to the figures, a prosthetic hip implant 1 having a body with stem 2 and neck 3 is illustrated. A collar 4 projects from stem 2 in the manner illustrated and as is well known in the art. A through bore 5 is provided in the uppermost portion of stem 2 for engagement with an extraction instrument as is also known in the art. Stem 2 of implant 1 includes a proximal end 6, a distal end 7, and a air of approximately opposite sidewalls 8 separated by a medial wall 9 and a lateral wall 10. Stem 2 further includes a polymer coating 11 preferably of polymethylmethacrylate (PMMA) near proximal end 11 and a polymer coating 12 also preferably of PMMA near distal end 7. The polymer coatings 11, 12 contact with bone cement during impaction of the implant to achieve a chemical bond therebetween. The polymer coating is substantially completely polymerization as a coating on the hip prosthesis prior to implantation. During impaction of the implant with fresh bone cement at the time of surgery, the polymer coatings 11, 12 will become securely bonded to the fresh bone cement as the fresh bone cement polymerizes. A more thorough explanation of the polymer coating and its reaction with the fresh bone cement may be obtained by a reading of Crowninshield et al. U.S. Pat. No. 4,795,472 issued and incorporated herein by reference.

It is highly desirable during impaction to position stem 2 of implant 1 within the medullary canal such that a cement mantle of a predetermined thickness is between the stem and canal wall. Therefore, spacers 20 are provided and are attached to implant 1 as by ultrasonic welding to bond the spacers to the polymer coating 11. The spacers of the invention formed in a variety of thicknesses to provide a variety of cement mantle thicknesses as may be desired by a particular surgeon.

Spacers 20 are preferably formed from PMMA, such as by injection molding. The advantages of forming spacers from PMMA are thoroughly discussed in Lewis et al. U.S. Pat. No. 4,566,138, issued and incorporated herein by reference. As illustrated, spacers 20 of the referred embodiment of FIGS. 1-6 are essentially tear-drop shaped and include a leading or frontal portion 22 and a rearward or trailing portion 24. Frontal portion 22 and rearward portion 24 are defined with reference to the insertion direction of the stem. Spacers 20 further include an inner wall 26 and an arcuate outer wall 28. Inner wall 26 is illustrated in FIG. 6 as being substantially flat but may be also contoured to conform to its intended supporting surface on the implant. An energy absorbing rib 30 extends outwardly from wall 26 prior to connection of the spacers to the implant. During ultrasonic welding rib 30 of spacer 20 is essentially melted to bond the spacer to the polymer coating 11, 12 on the implant. A more thorough understanding of ultrasonic welding of spacers to a prosthetic implant may be had by a reading of U.S. Pat. No. 4,566,138 previously incorporated by reference.

As can be readily seen by reference to FIGS. 1-6, the trailing portion 24 of a spacer 20 is tapered or narrows with distance from frontal portion 22. Spacers 20 are oriented such that frontal portion 22 of the spacers initially contacts the fresh cement within an intramedullary canal as the implant with spacers attached is inserted. Further, insertion of the implant with spacers attached into the canal causes cement to flow over outer wall 28 of the spacers. Due to the tapered design of trailing portion 24, cement flow along the outer wall 28 of the spacer smoothly re-attaches to the outer wall of the implant without creating undesired vortices in the cement. As is shown best in the spacer side view of FIG. 5, the spacer is formed having a diminishing thickness and diminishing width from frontal portion 22 toward trailing portion 24 similar to a cross-sectional view of a typical airfoil. This configuration of the spacer causes the cement to smoothly flow over outer wall 28 and re-attach to the implant surface without creating a substantial disturbance or vortex in the cement.

Contact between an outer wall 28 of a spacer 20 and the inner wall of the intramedullary canal (not shown) ensures a predetermined minimum thickness of cement between the stem of the implant and the supporting bone. With a spacer attached to each wall of the distal end of the implant, the spacers act to center the distal tip of the implant within the canal. Similarly, a spacer attached to each wall of the implant adjacent the proximal end acts to center the proximal end of the implant within the intramedullary canal. However, it should be understood that while the invention is illustrated as including a spacer on each wall of the implant, design criteria may dictate use of spacers on only one or some of the side walls. Such a modification should be considered enveloped in this disclosure.

An alternative embodiment of a spacer is illustrate in FIG. 7. As is clearly illustrated, spacer 32 includes a generally diamond shaped periphery having a thickened mid-portion 34 which gradually tappers off in all directions. An extension leading point 36 and a trailing point 35 is defined which causes the cement to smoothly flow over the outer surface of the spacer to smoothly re-attach to the supporting prosthetic implant. The tapered leading point 36 provides a smooth transition of the cement onto the outer surface 33 of spacer 32. Trailing point 35 provides for the smooth re-attachment of the cement flow from the spacer onto the outer surface of the implant. While not illustrated, it should be understood in keeping with the disclosure above that a rib (not shown) may be formed on the inner wall of spacer 32 for bonding the spacer to the polymer coating during ultrasonic bonding.

It should also be understood that while the invention is illustrated in conjunction with a prosthetic hip stem this should not be considered limiting to the disclosure. Clearly the invention is equally applicable to any stemmed prosthetic implant inserted into a cement filled intramedullary canal such as is experienced in the field of prosthetic knee or other such joints.

Further, it should be understood that any accepted method of bonding the spacers to the implant may be employed while keeping within the teachings of this invention.

Finally, it should be understood that the invention is not to be limited to the details above, but may be modified within the scope of the appended claims.

We claim:

1. A spacer for connection to one outer wall of a prosthetic implant having a plurality of walls for spacing said one outer wall a predetermined distance from an inner wall of a canal when said implant is positioned within the canal, said spacer comprising a body having a frontal portion and a trailing portion, said spacer narrowing with distance from said frontal portion toward said trailing portion, said body further including a mounting surface adapted for contact with said prosthetic implant, said mounting surface of said spacer is adapted to contact only said one outer wall of said prosthetic implant.

2. The spacer of claim 1, further including means extending from said mounting surface for connecting said spacer to said implant.

3. The spacer of claim 1 wherein the spacer includes an outer surface which is generally arcuate.

4. The spacer of claim 1 wherein said spacer includes an extension projecting from said frontal portion opposite said trailing portion, said extension narrowing with distance from said frontal portion.

5. The spacer of claim 1 wherein the spacer is substantially tear-drop shaped.

6. The spacer of claim 4 wherein the spacer has a substantially diamond shaped periphery.

* * * * *